United States Patent [19]
Thomas

[11] 3,946,102
[45] Mar. 23, 1976

[54] LIQUID OCTA 2-LOWER ALKOXY ETHOXIDES OF ALUMINUM AND (MAGNESIUM OR CALCIUM)

[75] Inventor: Ian M. Thomas, Temperance, Mich.

[73] Assignee: Owens-Illinois, Inc., Toledo, Ohio

[22] Filed: July 26, 1974

[21] Appl. No.: 492,346

Related U.S. Application Data

[62] Division of Ser. No. 313,662, Dec. 11, 1972.

[52] U.S. Cl.............................. 423/600; 260/448 AD
[51] Int. Cl.$^2$............................................ C01F 7/16
[58] Field of Search............... 423/600; 260/448 AD

[56] References Cited
UNITED STATES PATENTS

| | | | |
|---|---|---|---|
| 3,413,083 | 11/1968 | Daenchlaker | 423/600 |
| 3,510,272 | 5/1970 | Schmank et al. | 423/600 |
| 3,759,683 | 9/1973 | Dislich et al. | 423/600 |
| 3,786,137 | 1/1974 | Thomas | 423/600 |

*Primary Examiner*—Herbert T. Carter
*Attorney, Agent, or Firm*—Robert F. Rywalski; Edward J. Holler

[57] ABSTRACT

Alkoxy ethoxides, for example 2-methoxy ethoxide, of aluminum and magnesium or aluminum and calcium, are provided. These compounds are of the formula $MAl_2(O-CH_2-CH_2-O-R)_8$ wherein M is calcium or magnesium and wherein R is an alkyl of 1 to 4 carbon atoms; they are liquids at about 25°C. and about 1 atmosphere of pressure and are produced by reacting aluminum and magnesium or calcium with mono-alkyl ethers of ethylene glycol. Methods for hydrolyzing the compounds to obtain oxides of the formula $MgAl_2O_4$ and $CaAl_2O_4$ are disclosed. For example, magnesium aluminum octa-(2 methoxy ethoxide) is produced, using ethylene glycol monomethyl ether (methyl "Cellosolve") as a reagent; the material is hydrolyzed and heated to form $MgAl_2O_4$.

6 Claims, No Drawings

LIQUID OCTA 2-LOWER ALKOXY ETHOXIDES OF ALUMINUM AND (MAGNESIUM OR CALCIUM)

This is a division of application Ser. No. 313,662, filed Dec. 11, 1972.

THE INVENTION

This invention relates to compositions containing aluminum and magnesium, or calcium, and more particularly it relates to magnesium-aluminum or calcium-aluminum octa-[2 alkoxy ethoxides] of the formula $MAl_2(O-CH_2-CH_2-O-R)_8$ wherein R is an alkyl of 1 to 4 carbon atoms and M is magnesium or calcium.

U.S. Pat. No. 3,510,272 discloses the hydrolysis of magnesium aluminum isopropoxide, or isopropylate, and other calcium aluminum alcoholates and magnesium aluminum alcoholates wherein the alcoholate or alkoxide group contains 2 to 5 carbon atoms. U.S. Pat. No. 3,413,083 discloses the production of mixed oxides by the use of separate alcoholates of different metals. This patent also indicates the formation of barium titanate by hydrolysis and calcination of $BaTi(OR)_6$. U.S. Pat. No. 3,637,406 claims that aluminum isopropoxide and magnesium isopropoxide are sources of alumina and magnesia respectively. It is also known that magnesia spinel can be formed when the sources of magnesia and alumina are magnesium hydroxide, or hydrate, and aluminum hydroxide, or hydrate. See, for example, U.S. Pat. No. 3,304,153, U.S. Pat. No. 2,805,167, and U.S. Pat. No. 3,565,646, U.S. Pat. Nos. 2,593,314 and 2,570,058 disclose the production of hydrated magnesia from certain magnesium alcoholates. U.S. Pat. No. 2,776,188 discloses a process for forming metal oxide gels by spraying hydrolyzable metal compounds into an atmosphere of steam or water vapor; the hydrolyzable metal compounds include aluminum alcoholates, phenolates and cresylates of aluminum, magnesium, zinc, titanium, calcium, chromium, manganese, etc., or alloys thereof. U.S. Pat. No. 1,689,356 discloses techniques for forming complex alcoholates such as, for example, magnesium aluminum ethylate. U.S. Pat. No. 2,917,366 discloses the reaction of aluminum trialkoxides with polyhydric alcohols to form a polymeric specie which is then converted to alumina. U.S. Pat. No. 3,631,083 discloses the reaction of $Mg(OR)_2$ and $Al(OR)_3$ wherein R is alkyl to $C_4$ and polyhydroxy compounds in the presence of water to form complexes thereof. U.S. Pat. No. 3,657,361 discloses the formation of compounds of the formula $Mg(OR)_2 \cdot (ROH)_n$ wherein n is a number from 0 to 3, preferably 0 3, and R is an alkyl radical having 1 to 3 carbon atoms or a radical of the general formula $-R_1-O-R_2$ wherein $R_1$ is an alkylene radical and $R_2$ is an alkyl radical with $R_1$ and $R_2$ having a total of 3 to 4 carbon atoms; various activators such as orthoformic acid esters, p-toluene sulfonic acid, iodine, halogens and other materials are disclosed whereby the reaction is effected.

Thus, from the foregoing, it will be seen that none of the above patents discloses the formation of aluminum and magnesium or aluminum and calcium octa-[2 lower alkoxy ethoxides], nor do they disclose that these compounds are liquids at about 25° C. and 1 atmosphere of pressure. Similarly, none of these references discloses that these compounds can be formed by reacting aluminum and magnesium, or calcium, with mono lower alkyl ethers of ethylene glycol to form these compounds or that the compounds can be hydrolyzed to form high purity, substantially anhydrous, amorphous oxide compositions corresponding to the formula $MgAl_2O_4$ or $CaAl_2O_4$, or the crystalline forms, i.e., magnesium or calcium spinels.

Thus, in accordance with one aspect of this invention, there are provided, as compositions of matter, compounds which are liquid at about 25° C. and about 1 atmosphere of pressure wherein the compounds are of the formula $MAl_2(O-CH_2-CH_2-O-R)_8$ wherein M is calcium or magnesium and R is a $C_1$ to $C_4$ alkyl, such as, for example, methyl, ethyl or normal butyl. The liquid nature of these products allows them to be more conveniently handled than solid aluminum and magnesium, or aluminum and calcium, alcoholates. The present materials are also easily distilled to produce highly pure products.

In accordance with another feature of this invention, $MAl_2(O-CH_2-CH_2-O-R)_8$ compounds, as described above, are produced by heating, between about ambient temperature and reflux, but preferably at reflux, calcium or magnesium and aluminum and a compound of the formula $R-O-CH_2-CH_2-O-H$ wherein R is a $C_1$ to $C_4$ alkyl so as to effect reaction and formation of the desired compounds, which compounds are then separated from the reaction mass, e. g. by distillation. The reaction will typically be conducted to substantial completion and it is found that quite desirable reaction rates are obtained. In contrast to magnesium, or calcium, aluminum alkoxides or alcoholates, wherein the alkoxide or alcoholate group is a $(-OR)$ group supplied by alkyl alcohols $(ROH)$, it will be found that the present reaction will typically proceed at a rate slightly slower than the rate obtained when normal alkyl alcohols are employed but at a rate significantly faster than when secondary alkyl alcohols are used and even more substantially at a faster rate when contrasted to tertiary alkyl alcohols. The alcoholates formed with normal alkyl alcohols are solid alkoxides of aluminum and calcium or magnesium. Thus, the present invention allows for the production of liquid compounds which, as indicated previously, are much more convenient for utilization than solids. When the alcoholates are formed from certain secondary alkyl alcohols, liquid products are produced; the present invention, however, has the advantage that the process for the formation of the liquid compounds involved herein proceeds at a substantially faster rate than when secondary alkyl alcohols are employed as reagents. Thus, liquid products can be produced in a more economical manner with much faster reaction rates. When tertiary lower alkyl alcohols are employed to form alcoholates or alkoxides, the reactions are extremely long and impractical; thus, the present invention has a superior advantage in that it is a much shorter reaction.

In the preferred manner of practicing the invention, magnesium (or calcium) and aluminum are reacted with a compound of the formula $R-O-CH_2-CH_2-OH$ at the reflux temperature of the system. This is done by heating the reaction mass and maintaining the reflux condition until the reaction is substantially complete. It will also be found that the reaction rate is sufficient so that there is no need to employ any reaction promoters to obtain desirable rates. That is, the method can be practiced in the absence of catalysts or activators. Preferably, the reaction is conducted with an excess of the stoichiometric amount (hereinafter also referred to as stoichiometric excess) of the compound of the formula $RO-CH_2-CH_2-O-H$ and quite convenient proportions will be found to be in excess of about 4 to about 8 moles of said compound per gram atom of aluminum employed. Aluminum 2-lower alkoxy ethoxides are somewhat similar in volatility to the calcium (or magnesium) aluminum octa (2-lower alkoxy ethoxides), thereby making separation difficult; magnesium (or calcium) 2-lower alkoxy ethoxides are much less volatile than the aluminum and magnesium (or calcium) compounds, thereby allowing the latter compounds to be easily separated from the former if present. Consequently, it will be desirable to use a stoichiometric amount of slight deficiency of aluminum relative to the calcium or magnesium. Thus, suitable proportions would be about 2 gram atoms of aluminum per gram atom of calcium (or magnesium), or less, for example about 1.9 to about 2 moles of aluminum per gram atom of magnesium or calcium, with quite excellent results being obtained using a ratio of about 1.95 to about 2:1, for example 1.97. Stoichiometric amounts for the reaction are 1 gram atom of Mg or Ca, 2 gram atoms of Al and 8 moles of R—O—CH$_2$—CH$_2$—OH After the reaction has gone to substantial completion, there will remain a solution of the MAl$_2$(O—CH$_2$—CH$_2$—O—R)$_8$ compound in the excess of the R—O—CH$_2$—CH$_2$—O—H compound. Following conventional techniques, the excess of the latter material will be removed, for example, by volatilization or distillation and then the desired compound will be separated from the residual material, preferably by distilling it off. Usually, it will be convenient to use high vacuums for the volatilization, such as, for example, pressures of about 1 millimeter of mercury or less.

The compounds of the formula MAl$_2$(O—CH$_2$—CH$_2$—O—R)$_8$, wherein M is calcium or magnesium and R is a C$_1$–C$_4$ alkyl, are hydrolyzable compounds and consequently are convenient sources for the production of compounds of the formula MgAl$_2$O$_4$ or CaAl$_2$O$_4$, that is, the spinels. Thus, in accordance with another feature of this invention, the aluminum and calcium or magnesium octa [2-lower alkoxy ethoxides] are added to a non-polar organic solvent, such as, for example, higher alkanes, like heptane, or aromatic compounds, like benzene, so as to form a solution and then this solution is combined with water so as to hydrolyze the compound and form a hydrolyzed precipitate. For quantitative conversions to the hydrolyzed precipitate, at least 6 moles of water will be employed per mole of the aluminum and calcium or magnesium octa [2-lower alkoxy ethoxide] compound. Usually, amounts of water in excess of this amount, for example, the theoretical stoichiometric amount of about 8 moles of water, will be employed or for that matter, excesses can be used up to 10 moles of water or even more. After the hydrolyzed precipitate is formed, the volatiles which will include the solvent employed and also the by-product 2-alkoxy ethanols, are separated, for example by filtration, leaving as a residue the hydrolyzed precipitate. This precipitate is then typically dried to a particulate mass such as, for example, by heating at 100° to 120° or 130° C or even higher for a time to dry same and then it is further heated to form an anhydrous, amorphous, small particle size, high surface area, high purity oxide product. The further heating of the dried product will typically be done at a temperature and for a time sufficient to remove residual carbon moieties, which carbon moieties may be present in the form of bound reaction product, residual 2-alkoxy ethoxide groups, which latter groups may be present notwithstanding the fact that more than a stoichiometric amount of water needed for full hydrolysis is employed, or even bound solvent; the heating will generally be done at a temperature less than about 700° C. so as to form a white, carbon free, anhydrous, amorphous, small particle size, high surface area, high purity oxide product. Typically, for example, as the dried, hydrolyzed product is heated, it will convert to a somewhat brownish colored material and at temperatures of about 400° C. it will convert to a substantially white colored particulate mass. Thus, for example, convenient temperatures to be employed to remove residual carbon moieties will be temperatures on the order of about 400° C. to less than about 700° C. for example, about 400° to 500° C. This resulting anhydrous, amorphous composition is of an extremely small particle size, typically having particles of the size of about 100 to 200 angstroms, has a surface area of about 300–400 square meters per gram and an extremely high purity level. For example, when using freshly distilled compounds of the formula MAl$_2$(O—CH$_2$—CH$_2$—O—R)$_8$ and high purity water, for example, distilled impurity levels of about 50 quarts per million or less of total other metal oxides are typically obtained, with no other single metal oxide being present in an amount greater than about 10 ppm by weight. These anhydrous amorphous, small particle size, high surface area, high purity oxide products are excellent supports for catalytic polymerization of olefins, especially polyethylene.

In order to convert the anhydrous, amorphous, small particle size, high surface area, high purity oxide product into a high purity, crystalline composition corresponding to the formula MgAl$_2$O$_4$ or CaAl$_2$O$_4$, all that is needed is to further heat the former product at a temperature and for a time sufficient to effect crystallization of the material. Thus, for example, the amorphous product can be consolidated or compacted into a solid unitary body, using conventional cold or hot pressing techniques and subjected to temperatures and times sufficient to convert the product to a crystalline, consolidated body of the formula CaAl$_2$O$_4$ or MgAl$_2$O$_4$ or, if desired, the particulate amorphous product, without being compacted or consolidated, can be so heated. It has been found that a temperature in excess of about 700° C. will be needed to effect conversions to the crystalline material.

While the foregoing generally describes hydrolysis wherein the products of the formula MAl$_2$(O—CH$_2$—CH$_2$—O—R)$_8$ were separated from the reaction mass in which they were formed and then added to another solvent and then hydrolyzed, this procedure may be varied. That is, according to another feature of this invention, magnesium or calcium and aluminum are reacted with a stoichiometric excess of a compound of the formula ROCH$_2$CH$_2$OH, preferably at the reflux temperature of the reaction mass, for a time sufficient to form a compound of the formula MAl$_2$(O—CH$_2$—CH$_2$—O—R)$_8$ and then this reaction mass, which will be a solution, is combined and contacted with water as described above so as to precipitate a hydrolyzed product and then the hydrolyzed product is dried, that is, separated from the bulk of the volatiles and then heated in the manner indicated above to form either anhydrous, amorphous, particulate products or heated still more to form either consolidated or particulate crystalline products of the formula CaAl$_2$O$_4$ or MgAl$_2$O$_4$.

While the invention has been described above with sufficient particularity to enable those skilled in the art to make and use same without an undue amount of experimentation and has indicated some of the best modes contemplated in practicing this invention, several examples follow. These examples are not to be construed as limiting and are set forth to further enable those skilled in the art to make and use the present invention.

EXAMPLE 1

According to the following procedure, magnesium aluminum octa-(2-methoxy ethoxide) is produced by using the monomethyl ether of ethylene glycol as a reagent. Into a reaction flask there are added about 250 grams of methyl "Cellosolve" and the reaction flask is equipped with a conventional soxhlet extractor. The thimble of the soxhlet extractor is previously charged with about 6.1 grams of magnesium turnings and about 13.5 grams of aluminum wire. The methyl Cellosolve is heated to reflux with stirring and a vigorous reaction soon starts with all of the magnesium being consumed in about 15 minutes and the aluminum in an additional 90 minutes to produce a fluid product which is a solution of the magnesium aluminum octa (2-methoxy ethoxide) in the excess methyl cellosolve. The fluid product is then evaporated under vacuum to remove excess methyl cellosolve and the liquid residue, which is the magnesium aluminum octa (2-methoxy ethoxide), is thereafter distilled from the reaction flask under vacuum (about 0.1 mm of mercury pressure and at a temperature of about 240° to 245° C.). The product is a pale yellow liquid and is obtained in about 90 percent yield.

About 150 grams of the distilled product are dissolved in about 800 cc of benzene to form a solution and the solution is then combined with distilled water to effect hydrolysis, the amount of water being about 8 moles of water per mole of product employed. A hydrated oxide precipitate is formed and is separated from the solution by filtration. The precipitate is then heated at about 120° C. for a time sufficient to evaporate the solvent and produce a dry particulate product; the dried product is further heated to remove residual carbon moieties. At temperatures between about 250°–300° C. end up to a temperature of about 400° C. the material is somewhat brown but at a temperature of about 400° C. it converts to a white, carbon free, anhydrous product. This product typically has particle sizes in the range of about 100 to 200 angstroms and a surface area typically of about 300–400 square meters per gram and typically contains less than about 50 parts per million total impurities. This product is amorphous and represents an excellent catalyst support for the production of olefin polymers and especially the production of polyethylene.

A portion of the particulate amorphous white material as produced above is then heated to a temperature of about 1200° C. and an analysis of the particulate product after heating to 1200° C. shows a composition generally corresponding to a molar ratio of $MgO:Al_2O_3$ of about 1.00:1.02, whereas the theoretical value for spinel ($MgAl_2O_4$ or $MgO \cdot Al_2O_3$) is 1:1. High quality, pure crystalline spinel bodies are easily formed using conventional techniques, such as compaction by means of pressing, wherein the material which is compacted is the amorphous particulate material described above and the compact then heated at a temperature and for a time sufficient to form a crystalline body. Typically it will be found that the amorphous product converts to crystalline spinel at a temperature of about 700° C.

EXAMPLE 2

Substantially similar results are obtained when practicing the procedure of Example 1 to produce magnesium aluminum octa (2-ethoxy ethoxide) using ethyl Cellosolve and magnesium aluminum octa (2-normal butoxy ethoxide) using n-butyl Cellosolve.

EXAMPLE 3

Following the general procedure of Example 1, calcium alluminum octa (2-methoxy ethoxide) is produced using a ratio of about 1.97 gram atoms of aluminum per gram atom of calcium and about 6.5 moles of methyl Cellosolve per gram atom of aluminum. The liquid product is separated from the reaction medium in about a 96 percent yield at a boiling point of about 220° to 230° C. at a pressure of about 0.1 mm of mercury. The product is shown by analysis to be $CaAl_2(O-CH_2-CH_2-O-CH_3)_8$. When hydrolyzed as indicated in the manner set forth in Example 1, substantially similar results are obtained.

EXAMPLE 4

The general procedure of Example 1 is repeated using about 1.97 gram atoms of aluminum per gram atom of magnesium and about 6.5 moles of methyl Cellosolve per gram atom of aluminum but the excess Cellosolve and the resultant magnesium aluminum octa (2-methoxy ethoxide) is not separated after the synthesis reaction. Instead, the solution containing the $MgAl_2(O-CH_2-CH_2-O-CH_3)_8$ product in excess methyl Cellosolve is combined with about 8 moles of water to hydrolyze the magnesium-aluminum product, producing a hydrated oxide precipitate. This precipitate is then treated in the manner indicated in Example 1 with substantially similar results being obtained except the purity level may be lower. High purity levels are obtainable by using higher purity metals.

I claim:

1. The method for making an oxide product of the formula $MAl_2O_4$ wherein M is calcium or magnesium comprising the steps of combining a solution of a compound of the formula $MAl_2(O-CH_2-CH_2-O-R)_8$, wherein R is a $C_1$ to $C_4$ alkyl, in a polar organic solvent with at least about 6 moles of water per mole of said compound so as to hydrolyze said compound and form a hydrolyzed precipitate; separating said polar organic solvent and heating said hydrolyzed precipitate at a temperature and for a time sufficient to remove residual carbon moieties but at a temperature less than 700° C. so as to form an anhydrous, amorphous, small particle size, high surface area, high purity oxide product of the formula $MAl_2O_4$.

2. The method of claim 1 wherein said latter product is further heated at a temperature above about 700° C. for a time sufficient to convert said product to a particulate crystalline material of the formula $MAl_2O_4$ wherein M is a Ca or Mg.

3. The method of claim 2 wherein said crystalline product is $MgAl_2O_4$.

4. The method for forming an oxide of magnesium or calcium and aluminum which comprises reacting magnesium or calcium and aluminum with a stoichiometric excess of a compound of the formula $R-O-CH_2-CH_2-O-H$ wherein the ratio of the gram atoms of aluminum to maganesium or calcium is about 2:1 or less for a time sufficient to form a reaction mass containing a compound of the formula $MAl_2(O-CH_2-CH_2-O-R)_8$ wherein M is Ca or Mg and R is a $C_1$ to $C_4$ alkyl, combining the reaction mass as above with at least about 6 moles of water per mole of said $MAl_2(O-CH_2-CH_2-O-R)_8$ compound so as to precipitate a hydrolyzed product, separating said excess of said $R-O-CH_2-CH_2-O-H$ compound from said reaction mass, and heating said hydrolyzed product at a temperature and for a time sufficient to dry said product and remove residual carbon moieties but at a temperature less than about 700° C. so as to form an anhydrous, amorphous, particulate product of the formula $CaAl_2O_4$ or $MgAl_2O_4$.

5. The method of claim 4 wherein the ratio of the gram atoms of aluminum to magnesium or calcium is about 1.95 to about 2:1.

6. The method of claim 4 wherein said product is further heated at a temperature above about 700° C. for a time sufficient to form a crystalline, high purity, small particle size compound of the formula $CaAl_2O_4$ or $MgAl_2O_4$.

* * * * *